United States Patent
Mastri et al.

(10) Patent No.: US 9,616,185 B2
(45) Date of Patent: Apr. 11, 2017

(54) SYSTEM HAVING MULTIPLE PNEUMATICALLY SEALED TROCARS

(71) Applicant: SurgiQuest, Inc., Milford, CT (US)

(72) Inventors: Dominick Mastri, Bridgeport, CT (US); Raymond Y. Tang, Rosemead, CA (US); Ralph Stearns, Bozrah, CT (US); Kenneth Blier, Cheshire, CT (US)

(73) Assignee: SURGIQUEST, INC., Milford, CT (US)

( * ) Notice: Subject to any disclaimer, the term of this patent is extended or adjusted under 35 U.S.C. 154(b) by 243 days.

(21) Appl. No.: 14/670,652

(22) Filed: Mar. 27, 2015

(65) Prior Publication Data

US 2015/0196722 A1  Jul. 16, 2015

Related U.S. Application Data

(62) Division of application No. 13/606,824, filed on Sep. 7, 2012, now Pat. No. 9,017,281.

(51) Int. Cl.
*A61B 17/00* (2006.01)
*A61M 13/00* (2006.01)
(Continued)

(52) U.S. Cl.
CPC ..... *A61M 13/006* (2014.02); *A61B 17/00234* (2013.01); *A61B 17/3417* (2013.01);
(Continued)

(58) Field of Classification Search
CPC .... A61M 2205/3337; A61M 2039/229; A61M 39/22; A61M 2202/02;
(Continued)

(56) References Cited

U.S. PATENT DOCUMENTS

| | | |
|---|---|---|
| 3,934,576 A | 1/1976 | Danielsson |
| 4,722,725 A | 2/1988 | Sawyer et al. |
| (Continued) | | |

FOREIGN PATENT DOCUMENTS

| | | |
|---|---|---|
| CN | 101384286 A | 3/2009 |
| EP | 23 29 774 A1 | 6/2011 |
| (Continued) | | |

OTHER PUBLICATIONS

English Translation of Office Action issued Sep. 26, 2016 in connection with Application No. CN201380057474.3.
(Continued)

*Primary Examiner* — Kevin C Sirmons
*Assistant Examiner* — William Carpenter
(74) *Attorney, Agent, or Firm* — Locke Lord LLP; Scott D. Wofsy; Arpita G. Buesing

(57) ABSTRACT

A valve assembly and method are provided for selectively controlling a flow of pressurized fluid from a fluid source to trocar assemblies. The valve assembly includes a first coupling for a primary trocar assembly for directing pressurized fluid thereto, a second coupling for a secondary trocar assembly for directing pressurized fluid thereto, a third coupling for a source of pressurized fluid for directing pressurized fluid from the source to the first and second couplings; and at least one valve member to be operable in at least first and second operating positions, the first operating position directing pressurized fluid from the source to a coupled primary trocar assembly while preventing pressurized fluid from the source from flowing to at least a coupled secondary trocar assembly, and the second operating position directing pressurized fluid from the source to the coupled primary trocar assembly and to at least the coupled secondary trocar assembly.

6 Claims, 8 Drawing Sheets

(51) Int. Cl.
*A61M 39/22* (2006.01)
*A61B 17/34* (2006.01)
*A61B 90/00* (2016.01)
*A61M 1/00* (2006.01)

(52) U.S. Cl.
CPC ...... *A61B 17/3474* (2013.01); *A61B 17/3498* (2013.01); *A61B 90/02* (2016.02); *A61M 13/00* (2013.01); *A61M 13/003* (2013.01); *A61M 39/223* (2013.01); *A61B 2017/3419* (2013.01); *A61M 1/00* (2013.01); *A61M 2202/0225* (2013.01); *A61M 2205/07* (2013.01); *A61M 2205/3344* (2013.01); *A61M 2210/1021* (2013.01)

(58) Field of Classification Search
CPC .. A61M 39/105; A61M 13/00; A61M 13/003; A61M 1/00; A61M 2202/0225; A61M 2205/3344; A61M 39/223
See application file for complete search history.

(56) References Cited

U.S. PATENT DOCUMENTS

| | | | |
|---|---|---|---|
| 4,819,653 A | 4/1989 | Marks | |
| 5,168,901 A | 12/1992 | Marks | |
| 5,246,419 A * | 9/1993 | Absten | A61M 13/003 600/560 |
| 5,340,364 A | 8/1994 | Ghelli et al. | |
| 5,707,351 A | 1/1998 | Dorsey, III | |
| 5,766,211 A | 6/1998 | Wood et al. | |
| 7,182,752 B2 | 2/2007 | Stubbs et al. | |
| 7,285,112 B2 | 10/2007 | Stubbs et al. | |
| 7,338,473 B2 | 3/2008 | Campbell et al. | |
| 7,798,998 B2 | 9/2010 | Thompson et al. | |
| 7,806,870 B2 | 10/2010 | Mastri et al. | |
| 7,854,724 B2 | 12/2010 | Stearns et al. | |
| 8,257,297 B2 | 9/2012 | Mantell | |
| 8,584,701 B2 | 11/2013 | Duncan | |
| 2004/0153027 A1 * | 8/2004 | Mantell | A61M 13/003 604/23 |
| 2007/0088275 A1 | 4/2007 | Stearns et al. | |
| 2007/0244363 A1 * | 10/2007 | Sano | A61B 1/00039 600/158 |
| 2009/0137943 A1 * | 5/2009 | Stearns | A61B 17/3421 604/26 |
| 2010/0168779 A1 | 7/2010 | Redl et al. | |
| 2010/0185058 A1 | 7/2010 | Mastri et al. | |
| 2011/0030678 A1 | 2/2011 | Power et al. | |
| 2012/0150101 A1 | 6/2012 | Stearns et al. | |
| 2012/0209166 A1 | 8/2012 | Power et al. | |
| 2012/0245511 A1 | 9/2012 | Stearns et al. | |

FOREIGN PATENT DOCUMENTS

| | | |
|---|---|---|
| WO | WO-2007093778 A1 | 8/2007 |
| WO | WO-2008077080 A2 | 6/2008 |
| WO | WO-2009058124 A1 | 5/2009 |
| WO | WO-2010042204 A2 | 4/2010 |

OTHER PUBLICATIONS

U.S. Appl. No. 61/104,448, Stearns et al.
U.S. Appl. No. 60/923,917, Stearns et al.
U.S. Appl. No. 60/959,826, Stearns et al.
U.S. Appl. No. 60/875,436, Stearns et al.
U.S. Appl. No. 60/461,149, filed Apr. 18, 2003, Stubbs et al.
International Search Report dated Dec. 11, 2013, for International Application No. PCT/US2013/058192.
International Preliminary Report on Patentability dated Mar. 19, 2015 for International Application No. PCT/US2013/058192.
Supplemental Search Report issued Apr. 14, 2016 in connection with EP13835041.

* cited by examiner

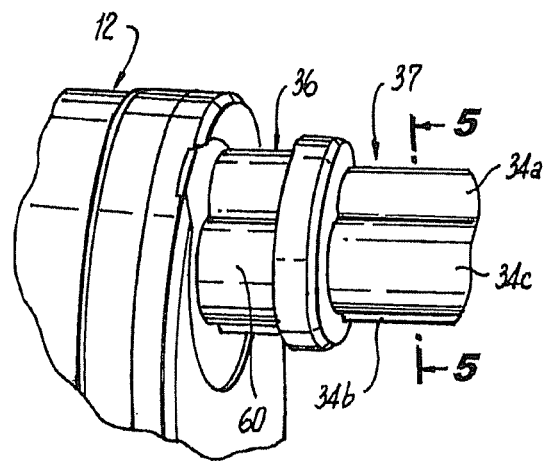
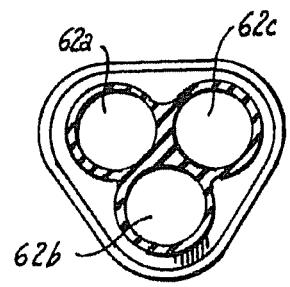
Fig. 4  Fig. 5
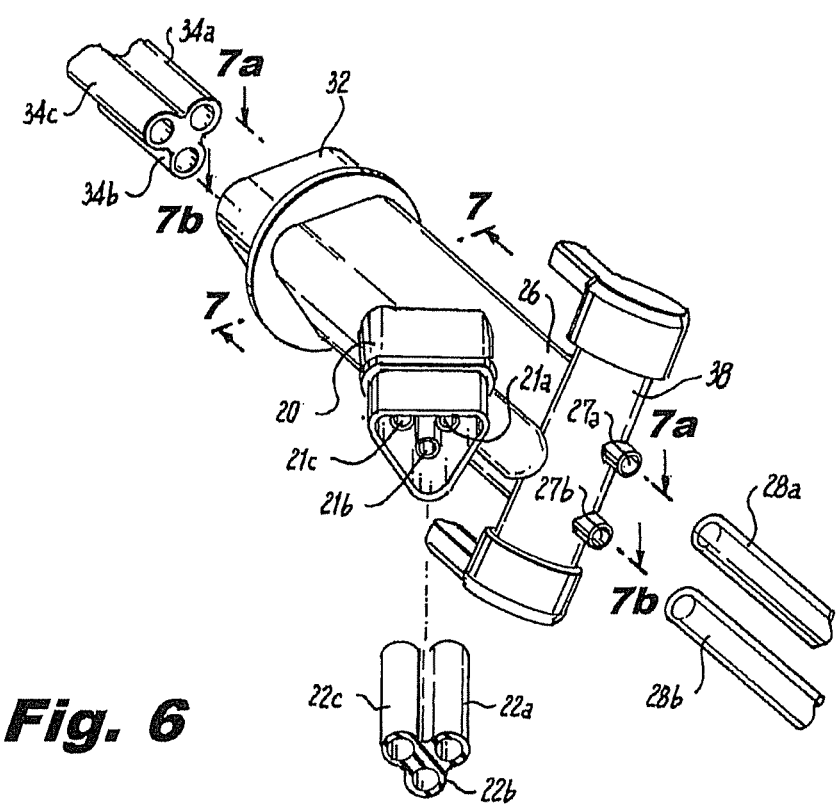
Fig. 6

SYSTEM HAVING MULTIPLE PNEUMATICALLY SEALED TROCARS

CROSS-REFERENCE TO RELATED APPLICATION

The present application is a divisional of U.S. patent application Ser. No. 13/606,824, filed on 7 Sep. 2012, now U.S. Pat. No. 9,017,281, issued on 28 Apr. 2015.

BACKGROUND OF THE INVENTION

1. Field of the Invention

The present invention relates to systems and methods for surgical access, and more particularly, to systems and methods for supplying pressurized fluid to surgical devices.

2. Description of Related Art

Laparoscopic, or "minimally invasive" surgical techniques are becoming increasingly more common. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable in order to maintain the pneumoperitoneum.

During typical laparoscopic procedures, a surgeon makes three to four small incisions which are usually no larger than about twelve millimeters each, and typically made with the trocar devices themselves by using a separate inserter or obturator placed therein. Following insertion, the inserter is removed, and the trocar allows instruments to be inserted therethrough into the abdominal cavity. Typical trocars often provide means to insufflate the abdominal cavity so that the surgeon has an open interior space in which to work.

Once inserted, the trocar must provide a means to maintain the pressure within the cavity, which requires providing a seal between the trocar and the surgical instruments being used while allowing at least some freedom of movement of the surgical instruments. Such instruments can include, for example, scissors, grasping instruments, occluding instruments, cauterizing units, cameras, light sources, and other surgical instruments. Sealing elements and mechanisms are typically provided on the trocars to prevent the escape of insufflation gas. Sealing elements and mechanisms typically include a duckbill-type valve made of a relatively pliable material, and are configured to seal around an outer surface of surgical instruments passing through the trocar. However, sealing performed in this manner cannot seal between multiple instruments, and inhibits free movement of the surgical instruments and/or removal of tissue through the trocar. Such seals are also vulnerable to damage during the surgical procedure. Alternatively, a flapper valve or spring-loaded trap door can be used. However, these types of mechanical valves suffer from similar drawbacks.

Most valves, and particularly duckbill-type valves which include resilient valve members that directly contact surgical instruments, not only interfere with the movement of surgical instruments, but also reduce the ability of a surgeon to accurately sense the anatomy of the patient on which the surgeon is operating. While minimally invasive surgical procedures are carried out with a visualization aid such as a camera, the surgeon's depth perception is inhibited during the procedure. Moreover, when the endoscope passes through mechanical seals, the camera lenses thereof can be dirtied, typically with smears appearing, which results in further vision difficulty. In the absence of such mechanical seals, specimens can be extracted without excessive interference. Additionally, the ability of the surgeon to physically sense resistance of structures and tissues through movement of the surgical instruments plays an important role in the success and safety of the surgical procedure. Frictional forces imparted on surgical instruments by contact of the aforementioned mechanical valves can mask the sensory signals, i.e., the haptic perception, that the surgeon might otherwise use to determine precisely what is occurring at the opposite end of the surgical instruments being used.

One type of seal utilized more recently during surgical procedures is a fluidic or pneumatic seal provided in a trocar assembly coupled to a source of pressurized fluid. The trocar assembly is inserted into a cavity (e.g., the abdominal cavity) of a patient, and defines a lumen which provides access to the cavity. The pressurized fluid is directed to the lumen of the trocar assembly to provide a pneumatic seal within the lumen. In this manner, surgical instruments may be passed through the lumen and pneumatic seal and maneuvered within the body cavity. The pressurized fluid flows around the surgical instruments inserted therethrough, maintaining the pneumatic seal in the trocar assembly and a pressure differential between the body cavity of the patient and the outside environment while causing minimal friction forces on the surgical instruments as they are maneuvered through the trocar assembly at the operation site.

While conventional methods and systems for sealing technologies have generally been considered satisfactory for their intended purpose, there is still a need in the art for improved systems and methods which are easy to make and use for providing unencumbered access to a body cavity, and for operation of surgical access devices while maintaining the pneumoperitoneum created during insufflation.

SUMMARY OF THE INVENTION

The subject invention is directed to a new and useful valve assembly and method for selectively providing pressurized fluid to a plurality of trocar assemblies. The valve assembly includes a first coupling configured and adapted to couple to a primary trocar assembly for directing pressurized fluid thereto; a second coupling configured and adapted to couple to a secondary trocar assembly for directing pressurized fluid thereto; a third coupling configured and adapted to couple to a source of pressurized fluid for directing pressurized fluid from the source to the first and second couplings; and at least one valve member adapted and configured to be operable in at least first and second operating positions. In the preferred embodiment, the first operating position of the valve assembly directs pressurized fluid from the source to a coupled primary trocar assembly while preventing pressurized fluid from the source from flowing to at least a coupled secondary trocar assembly, and the second operating position of the valve assembly directs pressurized fluid from the source to the coupled primary trocar assembly and at least the coupled secondary trocar assembly.

In certain embodiments of the valve assembly, the first coupling defines three passageways, the second coupling defines two passageways, and the third coupling defines three passageways. The valve assembly couples to a first elongate tube which preferably defines three passageways configured to couple the primary trocar assembly with the three passageways of the first coupling. The valve assembly also couples to a second elongate tube which preferably defines two passageways configured to couple the secondary trocar assembly with the two passageways of the second coupling, and a third elongate tube which preferably defines three passageways, a first of which is configured to couple the source of pressurized fluid with a first of the three passageways of the third coupling.

In certain embodiments, the at least one valve member of the valve assembly includes an elongated shaft rotatable about a longitudinal axis to switch the valve assembly between the first and second operating positions. The elongated shaft preferably defines first and second apertures configured to be fluidly isolated from the second coupling of the valve assembly in the first operating position, and fluidly coupled to the second coupling of the valve assembly in the second operating position. The at least one valve member may alternatively be configured as a push pull valve.

According to one aspect of the invention, the at least one valve member includes a first handle member, the elongated shaft has a top end and a bottom end, and the first handle member is coupled to one of the top and bottom ends of the elongated shaft.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 4 is an enlarged view of the fluid source coupler of the valve assembly of FIG. 1;

FIG. 5 is a cross-sectional view of the fluid source coupler of FIG. 4;

FIG. 6 is an enlarged view of the first, second, and third couplings and valve of the valve assembly of FIG. 1;

FIG. 7a is a first cross sectional view of the first, second, and third couplings and the valve of FIG. 6 along line 7a.

DETAILED DESCRIPTION OF THE PREFERRED EMBODIMENTS

The present invention is now described more fully with reference to the accompanying drawings, in which an illustrated embodiment of the present invention is shown. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited. It must be noted that as used herein and in the appended claims, the singular forms "a", "an," and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Figure 1:
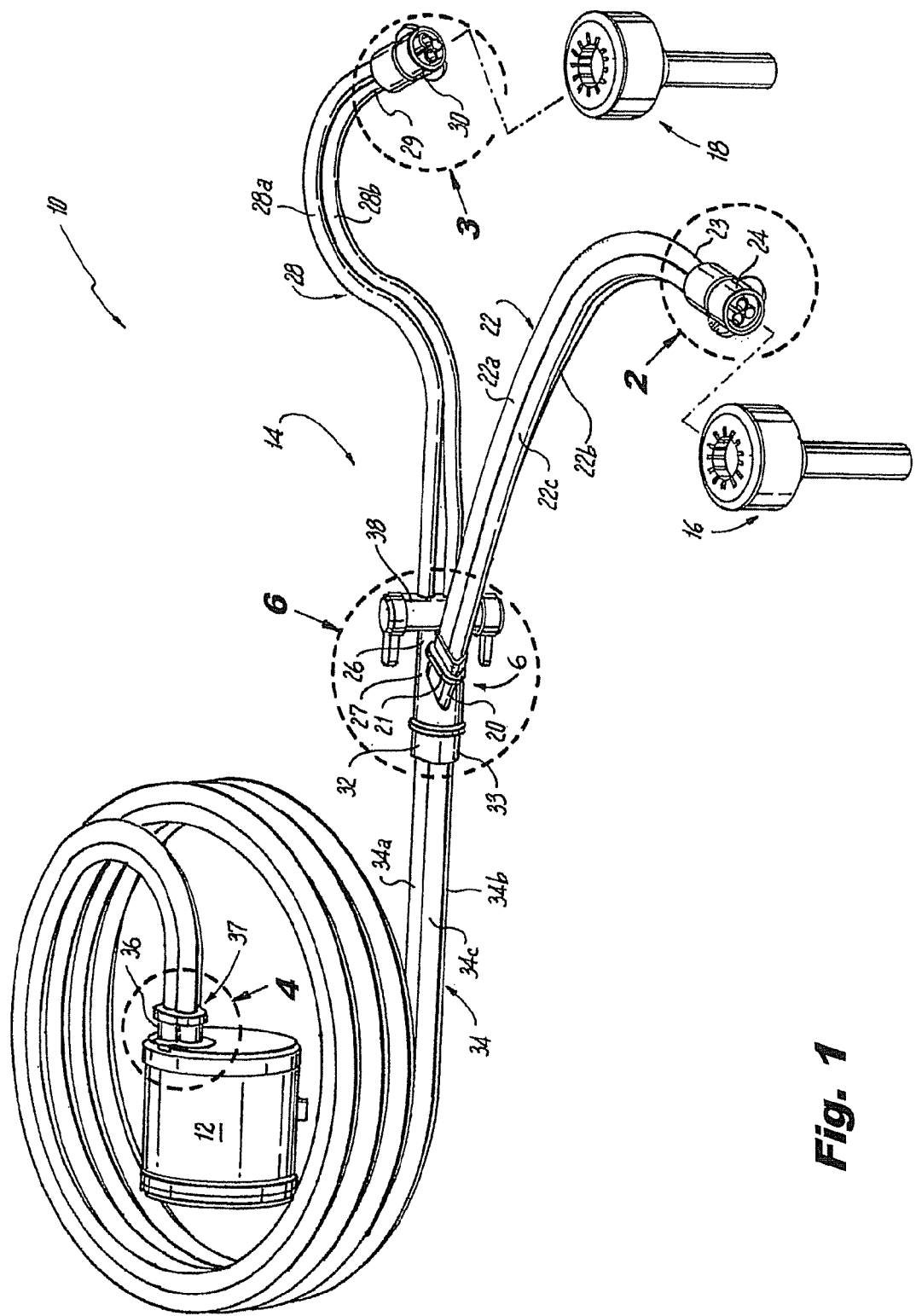
FIG. 1 is a perspective, partially exploded view of an exemplary embodiment of a valve assembly system constructed in accordance with an illustrated embodiment of the invention.

Starting with FIG. 1, shown is a partial view of an exemplary embodiment of a system in accordance with the invention, designated generally by reference character 10. The system 10 generally includes a valve assembly 14 coupled to a source 12 of pressurized fluid, the valve assembly 14 configured to selectively provide pressurized fluid from the source 12 to a primary trocar assembly 16 and a secondary trocar assembly 18 as described below.

Examples of systems and apparatuses which include a source of pressurized fluid used in conjunction with trocar assemblies adapted and configured to pierce the abdominal cavity and provide fluidic seals are set forth in the following applications and patents, all of which are incorporated herein by reference in their entireties: PCT/US09/005537, filed Oct. 9, 2009, U.S. Provisional Application No. 61/104,448, filed Oct. 10, 2008, U.S. patent application Ser. No. 11/960,701, filed Dec. 20, 2007, PCT/U.S.07/88017, filed Dec. 18, 2007, U.S. Provisional Application No. 60/923,917, filed Apr. 17, 2007, U.S. Provisional Application No. 60/959,826, filed Jul. 16, 2007, U.S. patent application Ser. No. 11/786,832, filed Apr. 13, 2007, U.S. Provisional Application No. 60/875,436, filed Dec. 18, 2006, U.S. patent application Ser. No. 11/544,856, filed Oct. 6, 2006, U.S. patent application Ser. No. 11/517,929, filed Sep. 8, 2006 (now U.S. Pat. No. 7,854,724), U.S. patent application Ser. No. 10/776,923, filed Feb. 11, 2004 (now U.S. Pat. No. 7,338,473), U.S. patent application Ser. No. 10/739,872, filed Dec. 18, 2003 (now U.S. Pat. No. 7,285,112), U.S. patent application Ser. No. 10/441,149, filed May 17, 2003 (now U.S. Pat. No. 7,182,752), and U.S. Provisional Application No. 60/461,149, filed Apr. 8, 2003. The various devices, systems, and methodologies disclosed in the above listed references may be utilized with the system 10.

The system 10 of the present invention is used in accordance with exemplary methodologies of the invention to insufflate the abdominal cavity of a patient, to selectively provide fluidic, pneumatic seals within the primary and secondary trocar assemblies 16, 18 using pressurized fluid from a single port of the fluid source 12, and to recirculate such pressurized fluid from the primary and secondary trocar assemblies 16, 18 back through the single port of the fluid source 12. The new and useful valve assembly 14 of the system 10 facilitates such operation and functionality, and is discussed below with respect to FIGS. 1-11. Operation of the system 10 in accordance with preferred methodologies of the invention is discussed below with respect to FIGS. 12-13.

Continuing now with FIG. 1, the valve assembly 14 includes a first coupling 20 configured to be coupled to a first elongate tube 22, a primary trocar coupler 24, a second coupling 26 configured to be coupled to a second elongate tube 28, a secondary trocar coupler 30, a third coupling 32 configured to be coupled to a third elongate tube 34, a fluid source coupler 36, and a valve member 38.

Figure 7:
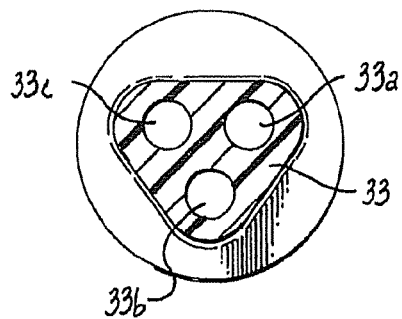
FIG. 7 is a cross sectional view of the third coupling of FIG. 6.
Figure 7A:
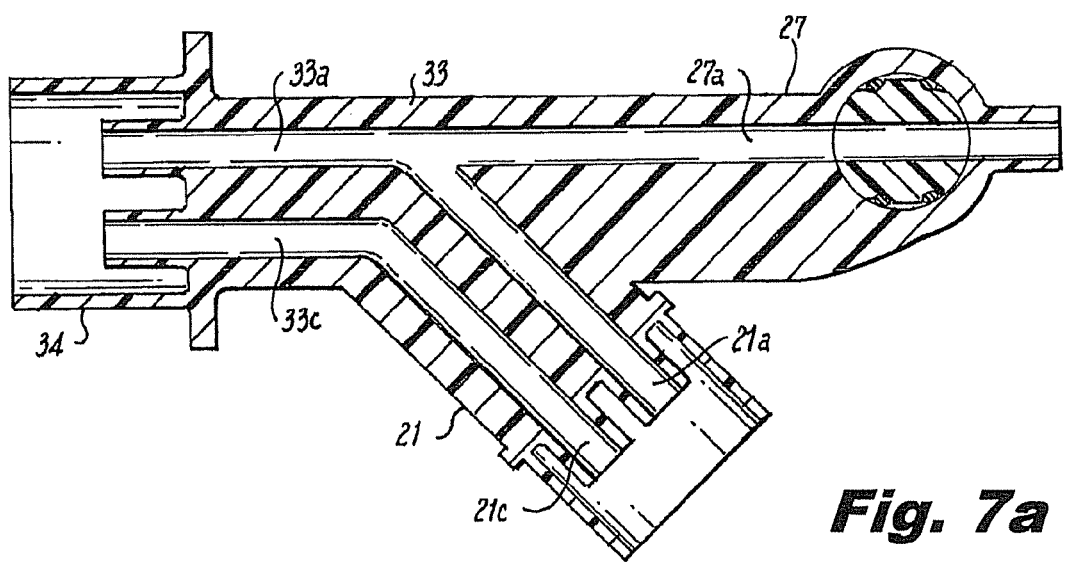
Figure 7B:
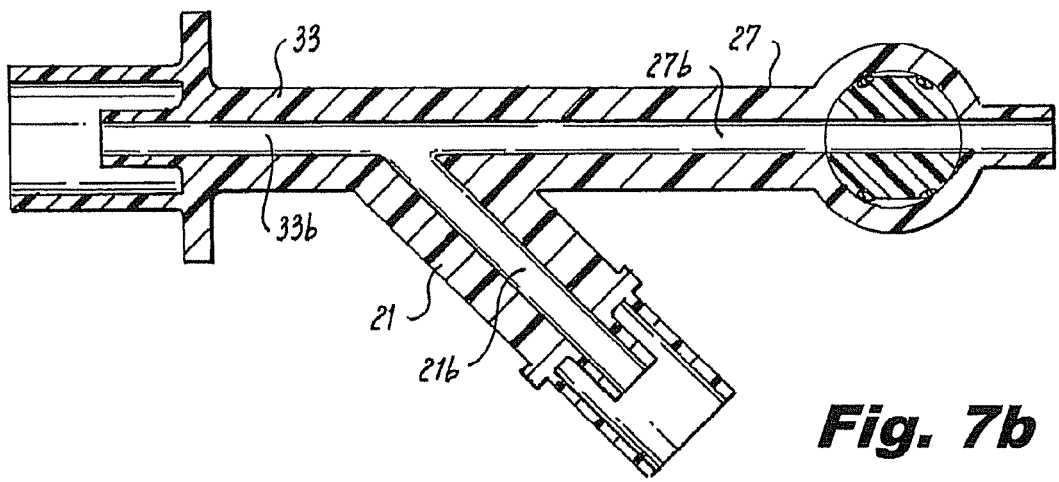
FIG. 7b is a second cross sectional view of the first, second, and third couplings and the valve of FIG. 6 along line 7b.

The first, second, and third couplings 20, 26, 32 and the valve member 38 of the valve assembly 14 together form a manifold 6 which is best shown in FIGS. 6-7b. The first coupling 20 includes a housing 21 which defines three passageways 21a, 21b, 21c, the second coupling 26 includes a housing 27 which defines two passageways 27a, 27b, and the third coupling 32 includes a housing 33 which defines three passageways 33a, 33b, 33c (FIGS. 7, 7a, 7b). The passageway 33a of the third coupling 32 is fluidly coupled with both the passageway 21a of the first coupling 20 and the passageway 27a of the second coupling 26. The passageway 33b of the third coupling 32 is fluidly coupled with both the passageway 21b of the first coupling 20 and the passageway 27b of the second coupling 26. The passageway 33c of the third coupling is fluidly coupled with the passageway 21c of the first coupling 20, but not with either of the passageways 27a, 27b of the second coupling 26. The housings 21, 27, 33 of the manifold 6 are preferably integrally formed with one another as a single integral unit, but may alternatively be detachably coupled to one another via threaded engagement, interference fit, or any other suitable means known in the art.

Continuing now with reference to FIGS. 1 and 6-7b, the first elongate tube 22 is preferably a trifurcated tube which defines three separate tubes 22a, 22b, 22c sized and configured to fluidly couple to the three passageways 21a, 21b, 21c of the first coupling 20 within the manifold 6, and to the primary trocar coupler 24 at an end 23 opposite the manifold 6. The second elongate tube 28 (FIG. 1) is preferably a bifurcated tube which defines two separate tubes 28a, 28b sized and configured to fluidly couple with the two passageways 27a, 27b of the second coupling 26 within the manifold 6, and to the secondary trocar coupler 30 at an end 29 opposite the manifold 6. The third elongate tube 34 is preferably a trifurcated tube which defines three separate tubes 34a, 34b, 34c sized and configured to fluidly couple with the three passageways 33a, 33b, 33c of the third coupling 32 within the manifold 6, and to the fluid source coupler 36 at an end 37 opposite the manifold 6. The primary trocar coupler 24, secondary trocar coupler 30, and fluid source coupler 36 detachably couple to, respectively, the primary trocar assembly 16, the secondary trocar assembly 18, and the fluid source 12.

Figure 2:
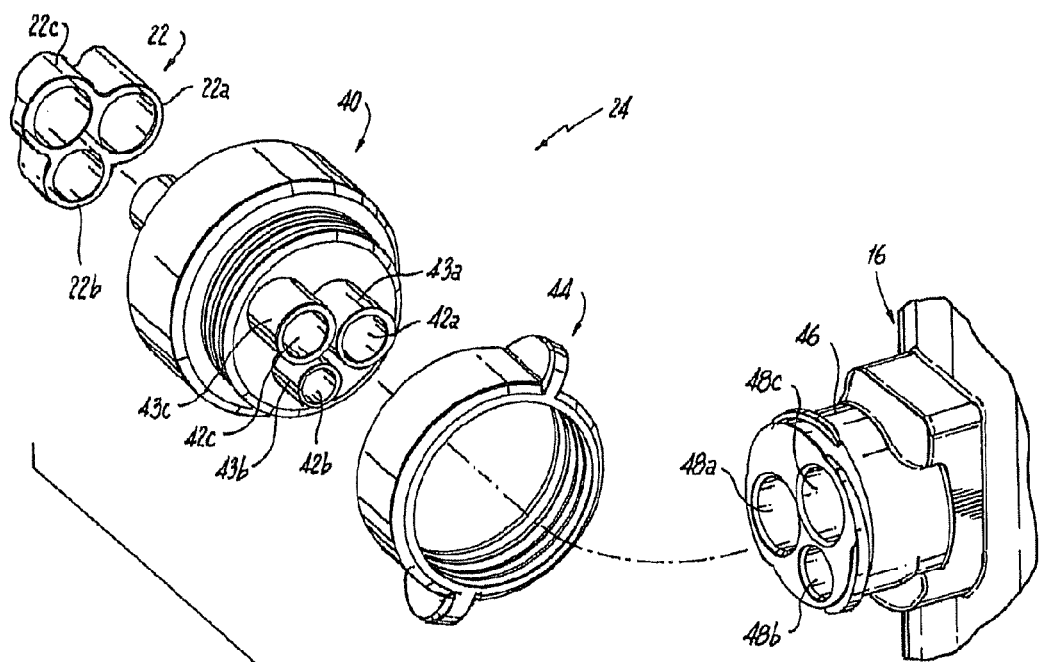
FIG. 2 is an enlarged exploded view of the primary trocar coupler of the valve assembly of FIG. 1.

Turning now to FIG. 2, the primary trocar coupler 24 includes an attachment body 40, three cylindrical passages 42a, 42b, 42c defined by annular walls 43a, 43b, 43c extending through and projecting from the attachment body 40 on opposite sides thereof, an attachment ring 44, and a receiving collar 46 mounted to the primary trocar assembly 16. The receiving collar 46 defines three passageways 48a, 48b, 48c sized and configured to receive the annular walls 43a, 43b, 43c and leading to respective chambers within the primary trocar assembly 16 where pressurized fluid is supplied and retrieved. The attachment ring 44 threadably couples the attachment body 40 to the receiving collar 46 with the passages 42a, 42b, 42c fluidly coupled with the passageways 48a, 48b, 48c. The tubes 22a, 22b, 22c of the first elongate tube 22 are detachably and fluidly coupled to the passages 42a, 42b, 42c on the side of the attachment body 40 opposite the ring 44. This configuration fluidly couples the trifurcated first elongated tube 22 to the primary trocar assembly 16.

Figure 3:
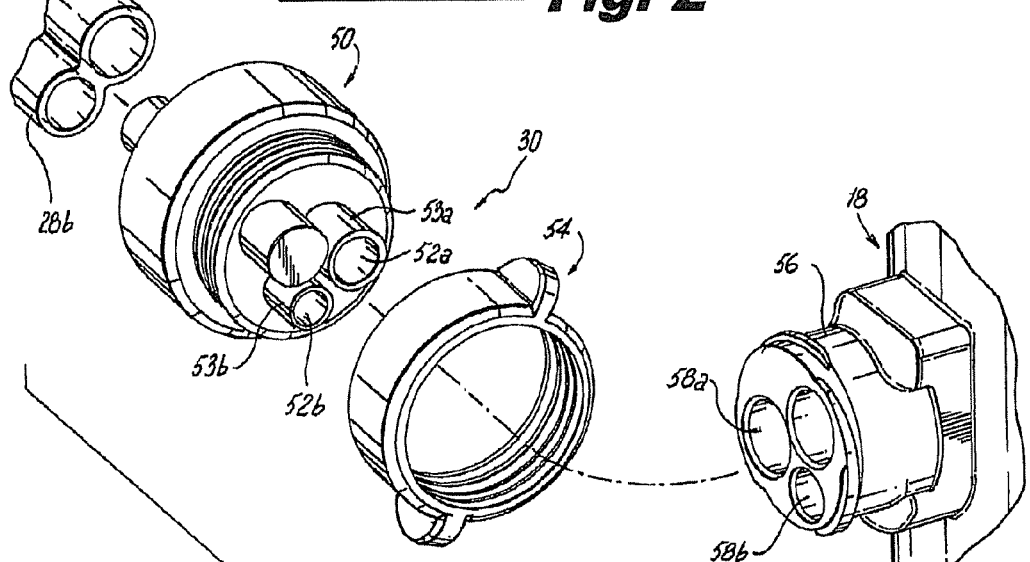
FIG. 3 is an enlarged exploded view of the secondary trocar coupler of the valve assembly of FIG. 1.

Turning to FIG. 3, the secondary trocar coupler 30 includes an attachment body 50, two cylindrical passages 52a, 52b defined by annular walls 53a, 53b extending through and projecting from the attachment body 50 on opposite sides thereof, an attachment ring 54, and a receiving collar 56 mounted to the secondary trocar assembly 18. The receiving collar 56 defines two passageways 58a, 58b sized and configured to receive the annular walls 53a, 53b and leading to respective chambers within the secondary trocar assembly 18 where pressurized fluid is supplied and retrieved. The attachment ring 54 threadably couples the attachment body 50 to the receiving collar 56 with the passages 52a, 52b fluidly coupled with the passageways 58a, 58b. The tubes 28a, 28b of the second elongate tube 28 are detachably and fluidly coupled to the passages 52a, 52b on the side of the attachment body 50 opposite the ring 54. This configuration fluidly couples the bifurcated second elongate tube 28 with the secondary trocar assembly 18.

Turning to FIGS. 4 & 5, the fluid source coupler 36 includes an attachment body 60 which defines three channels 62a, 62b, 62c coupled to and received by the fluid source 12, and configured to fluidly couple to the first, second, and third tubes 34a, 34b, 34c of the third elongate tube 34 at the end 37 thereof. This configuration fluidly couples the trifurcated third elongate tube 34 with the fluid source 12.

Figure 8:
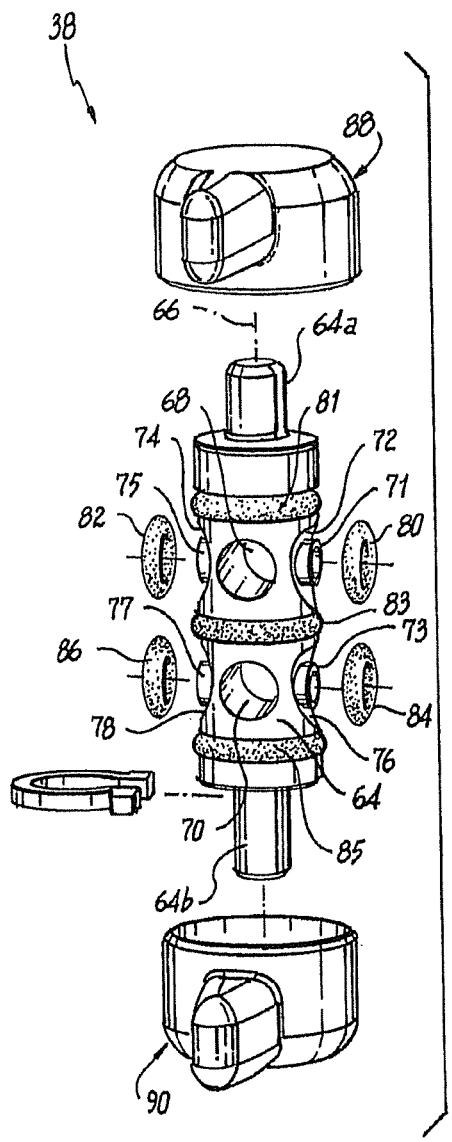
FIG. 8 is an enlarged exploded view of the valve of FIG. 6.

Turning now to FIG. 8, the valve 38 of the valve assembly 14 includes an elongated shaft 64 rotatable about a longitudinal axis 66. The elongated shaft 64 defines upper and lower apertures 68, 70 extending therethrough, upper concavities 72, 74 on opposite sides thereof, lower concavities 76, 78 on opposite sides thereof, and annular walls 71, 73, 75, 77 projecting from the concavities 72, 74, 76, 78. The concavities 72, 74, 76, 78 are configured to receive respective O-rings 80, 82, 84, 86 which are press-fit into the concavities 72, 74, 76, 78 over the annular walls 71, 73, 75, 77. The valve 38 also includes an upper handle 88 which couples to a upper end 64a of the elongated shaft 64, and a lower handle 90 which couples to a lower end 64b of the elongated shaft 64. The upper and lower ends 64a, 64b are of reduced diameter relative to the shaft 64, and may be integrally formed with the shaft 64 or detachably coupled thereto. Coupling of the handles 88, 90 to the upper and lower ends 64a, 64b may be achieved by any suitable means, such as, for example, threaded engagement, press-fit, glue adhesives, and the like. The shaft 64 is also provided with three additional O-rings 81, 83, 85 oriented concentrically relative to the longitudinal axis 66 of the shaft 64 around the outer surface of the shaft 64. The O-rings 81, 83, 85 preferably fit into circumferential grooves defined by the outer surface of the shaft 64. The O-rings 80, 81, 82, 83, 84, 85, 86 function to provide rotative resistance to the shaft 64 and fluid seals as further discussed below. Either of the upper and lower handles 88, 90 may be manipulated by a user to rotate the elongated shaft 64 of the valve 38 between the first and second operating positions shown in FIGS. 9 and 10.

Figure 9:
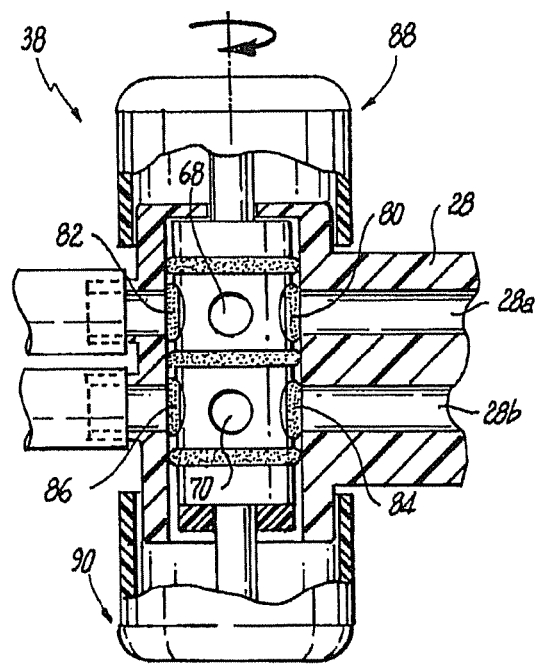
FIG. 9 is a cutaway view of the valve of FIG. 6.

Turning to FIG. 9, the valve 38 is shown operatively associated with and coupled to the second elongate tube 28 in the first operating position. In the first operating position, the upper and lower apertures 68, 70 are fluidly isolated from the two tubes 28a, 28b of the bifurcated tube 28. The O-rings 80, 81, 82, 83, 84, 85, 86 of the valve 38 interface to respective edges of the tubes 28a, 28b to provide rotational resistance to the elongated shaft 64 of the valve 38 via interference which can be overcome via manual manipulation of one of the handles 88, 90. In this manner, the O-rings 80, 81, 82, 83, 84, 85, 86 help maintain rotational position of the valve 38 in the first operating position of FIG. 9.

Figure 10:
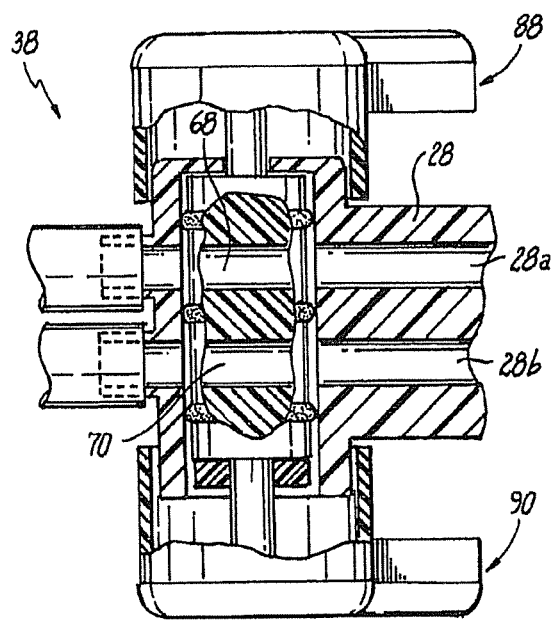
FIG. 10 is a cutaway view of the valve of FIG. 6.

Turning to FIG. 10, the valve 38 is shown operatively associated with and coupled to the second elongate tube 28 in the second operating position. In the second operating position, the upper and lower apertures 68, 70 are fluidly coupled with the two tubes 28a, 28b of the bifurcated tube 28. The O-rings 81, 83, 85, and O-rings 80, 82, 84, 86 (hidden from view in FIG. 10) of the valve 38 interface to respective edges of the tubes 28a, 28b on opposite sides thereof to help maintain the rotational position of the elongated shaft 64 of the valve 38 in the second operating position of FIG. 10 via interference. Such interference can be overcome via manual manipulation of one of the handles 88, 90. It will be appreciated that the O-rings 80, 82, 84, 86 also provide respective seals between the upper and lower apertures 68, 70 and the tubes 28a, 28b when the valve 38 is disposed in the second operating position. The valve 38 may be manually manipulated to move the valve assembly 14 between the first and second operating positions as further discussed below with respect to FIGS. 12-13.

Figures 11, 11A:
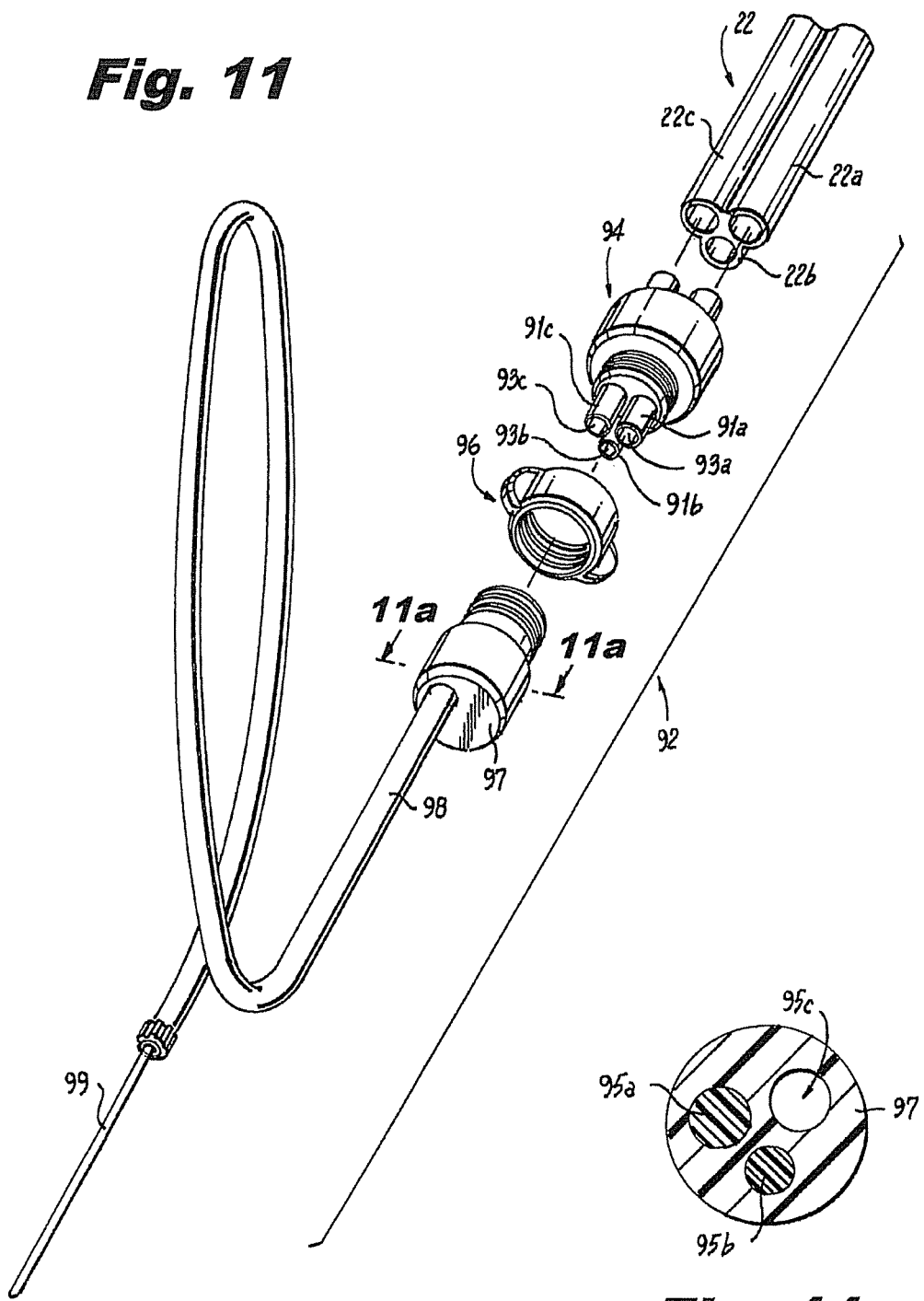
FIG. 11 is an exploded view of a veress needle assembly.
FIG. 11a is a cross sectional view of the coupling of the veress needle assembly of FIG. 11.

Turning now to FIGS. 11 and 11a the system 10 is also preferably used in conjunction with a veress needle assembly 92 which includes a connector body 94, collar 96, coupling 97, tube 98, and needle 99. The connector body 94 includes three annular walls 91a, 91b, 91c extending therethrough and projecting therefrom on opposite sides thereof. The annular walls 91a, 91b, 91c define passages 93a, 93b, 93c configured to fluidly couple with the three tubes 22a, 22b, 22c of the trifurcated first tubular member 22. The collar 96 threadably couples the connector body 94 to the coupling 97, which is fluidly coupled to the tube 98 via the lumen 95c. Plugs 95a, 95b projecting from the coupling 47 plug the passages 93a, 93b. Engagement of the connector body 94, collar 96, and coupling 97 fluidly couples the passage 93c with the tube 98 via lumen 95c and fluidly isolates the passages 93a, 93b from the tube 98 via the plugs 93a, 93b. As further discussed below, this configuration allows insufflation fluid to be translated from the passage 93c of the trifurcated first tubular member 22 to the tube 98 and the lumen of the needle 99 for insufflation of the abdominal cavity. The connector body 94, collar 96, and coupling 97 are preferably provided pre-assembled so that the surgeon need only connect the needle 99 to the tube 98.

Figure 12:
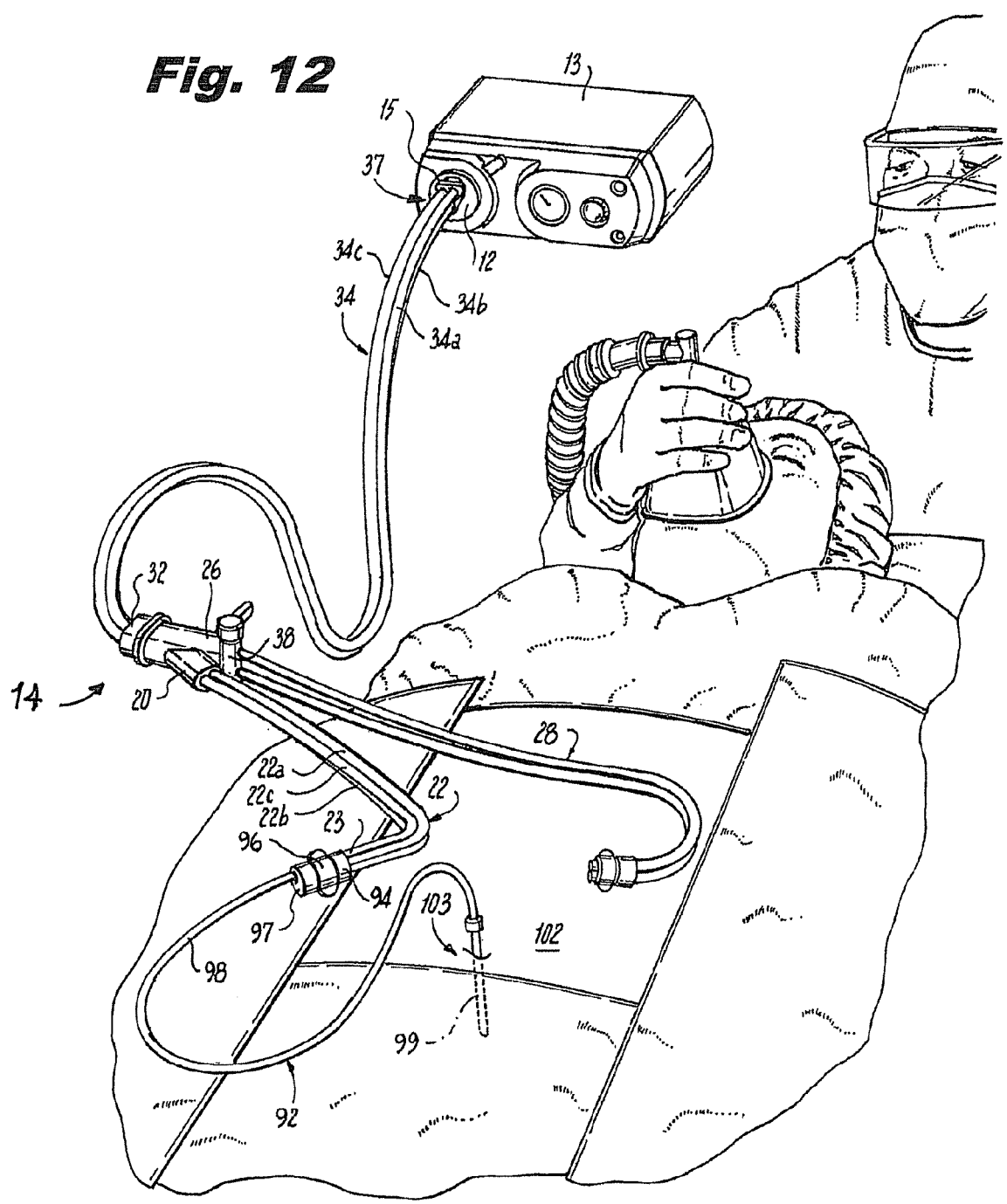
FIGS. 12 and 13 are perspective views of the system of the present invention being used during a surgical procedure.

With the structure of the present inventive system 10 being described above, its operation will now be described. Turning to FIG. 12, the valve assembly 14 of FIG. 1 is initially used to insufflate the abdominal cavity of a patient. Initially, the veress needle assembly 92 is coupled to the end 23 of the first elongate trifurcated tube 22 via the connector body 94 and collar 96 with the tube 22c fluidly coupled to the tube 98 and lumen (not shown) of the needle 99 and the tubes 22a, 22b fluidly isolated from the tube 98 and lumen of the needle 99. The first, second, and third elongate tubes 22, 28, 34 are coupled to the first, second, and third couplings 20, 26, 32 of the valve assembly 14, and the end 37 of the third elongate tube 34 is coupled to the fluid source 12. The fluid source 12 preferably includes a tank containing pressurized fluid (e.g., carbon dioxide gas), and is preferably mounted within and operably coupled to a control unit 13 and a pressure regulator for controlled operation thereof to controllably provide pressurized fluid through a single port 15.

With no pressurized fluid flowing through the port 15, the abdominal wall 102 of the patient is punctured using the needle 99 of the veress needle assembly 92, placing the tube 92 in fluid communication with the lumen of the needle 99. The control unit 13 is then operated to supply insufflation gas (e.g., $CO_2$) from the fluid source 12, through the tube 34c (insufflation line) via the port 15. Insufflation gas flows through the tube 34c, the passageway 33c of the third coupling 32 of the valve assembly 14, the passageway 21c of the first coupling 20 of the valve assembly 14, the tube 22c of the first elongate trifurcated tube 22, the passageway 93c (FIG. 11) of the connector body 94, the tube 98, and finally, through the lumen of the needle 99 into the abdominal cavity of the patient for insufflation thereof. The passageway 33c of the third coupling 32 is fluidly coupled to the passageway 21c of the first coupling 20, but not to any of the passageways of the second couplings 26. The valve 38 remains in the first operating position of FIG. 9.

The controller 13 preferably includes a pressure sensor which monitors pressure in at least the tube 34c, and automatically turns off or reduces the supply of insufflation gas when a predetermined pressure threshold is reached. The controller 13 may be also be manually operated to turn on, turn off, or reduce the supply of insufflation gas to the abdominal cavity during or after insufflation, though it is recommended that the controller 13 be inoperable to supply insufflation fluid once a predetermined maximum pressure is reached.

Once the predetermined pressure threshold within the abdominal cavity is reached, the connector body 94, collar 96, coupling 97, and tube 98, are detached from the needle 99 and the first elongate trifurcated tube 22. The needle 99 is removed from the patient, and the small incision left by the needle is sealed to prevent desufflation through the abdominal wall 102. Alternatively, if the needle is provided with a valve, then it may be left in the abdominal wall 102 with the valve in 'off' position to prevent desufflation of the abdominal cavity.

Figure 13:
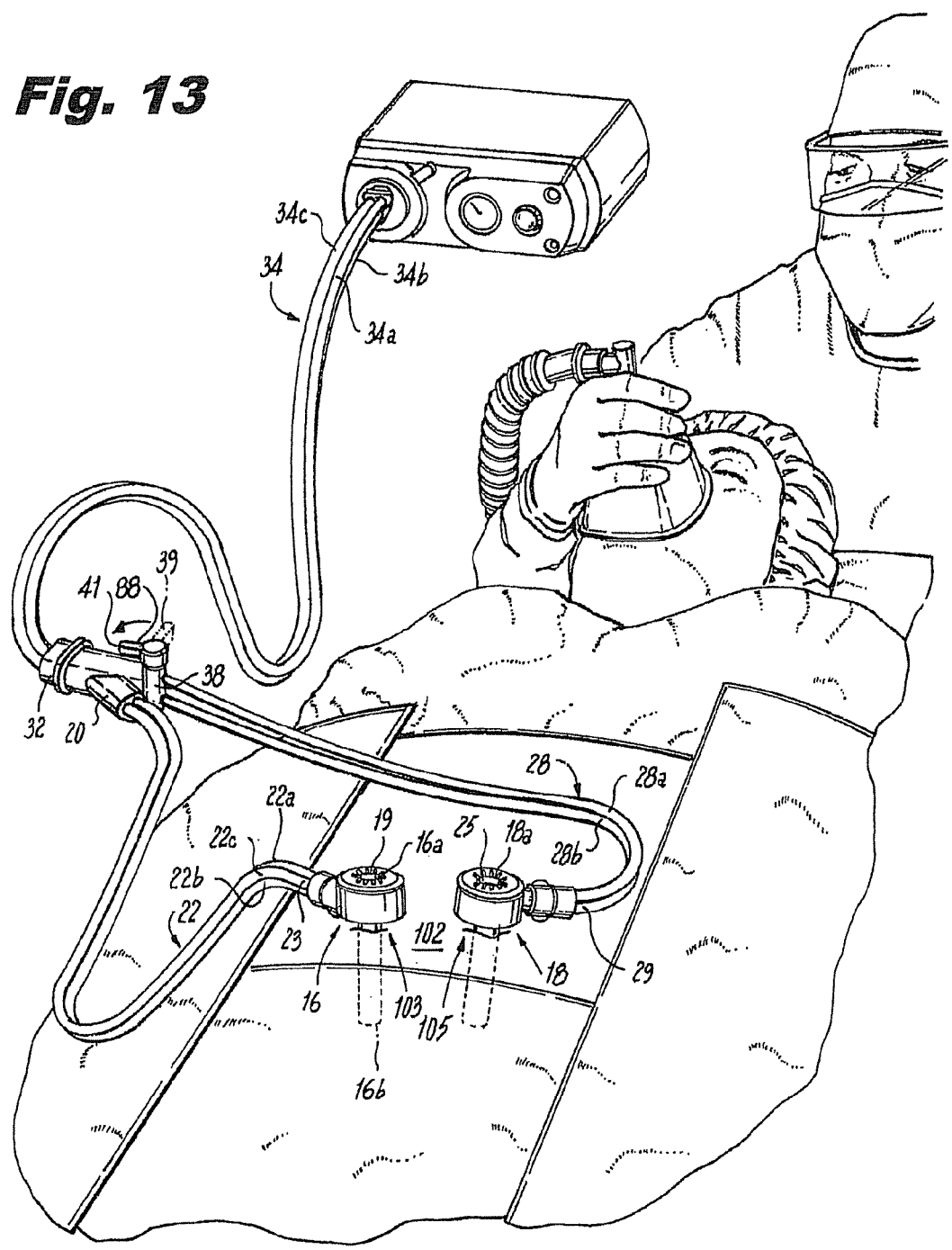

Turning to FIG. 13, the abdominal wall 102 is then punctured at a first location 103 using the primary trocar assembly 16, which preferably includes a cannula and obturator. The obturator is slidably inserted and translated through an opening 19 at a proximal end 16a of the primary trocar assembly and into and through the abdominal wall 12 at the first location 103. The distal end 16b of the primary trocar assembly 16 is then inserted through the incision in the abdominal wall 102 made by the obturator. A frictional fit/seal between outer diameter of obturator and an inner diameter of the cannula prevents desufflation through the primary trocar assembly 16.

The end 23 of the first elongate tube 22 is then attached to the primary trocar assembly 16 using the primary trocar coupler 24, thereby fluidly coupling each of the tubes 22a, 22b, 22c of the first elongate tube 22 with various chambers of the cannula of the primary trocar assembly 16. For example, tubes 22a, 22b, which correspond to the pressure/feed line and the vacuum/return line, are placed in fluid communication with a chamber of the cannula for, respectively, creation of a fluidic/pneumatic seal within the chamber and return/recirculation of gas that would otherwise exit through the opening 19 of the primary trocar assembly 16, and the sense/insufflation line 22c is placed in fluid communication with a separate chamber defined by the cannula which leads to the abdominal cavity of the patient in order to sense abdominal pressure within the abdominal cavity. The valve member 38 is initially maintained in the first operating position of FIG. 9, shown in FIG. 13 by the dotted position 39 of the top handle 88.

The control unit 13 is operated to supply pressurized gas from the fluid source 12 through the tube 34a (pressure line) of the trifurcated tube 34 via the port 15. The obturator of the primary trocar assembly 16 is then removed, and pressurized fluid (e.g., $CO_2$ gas) flows through the tube 34a, through the passageway 33a of the third coupling 32 of the valve assembly 14, the passageway 21a of the first coupling 20 of the valve assembly 14, the tube 22a of the first elongate trifurcated tube 22, the passageway 42a (FIG. 2) of the attachment body 40 of the primary trocar coupler 24, and the passageway 48a of the receiving collar 46 into a proximal chamber of the primary trocar assembly 16. While pressurized gas is supplied to the chamber of the primary trocar assembly 16, gas is simultaneously retrieved therefrom via the tube 22b. In particular, the retrieved gas flows from the chamber of the primary trocar assembly 16, through the passageways 48b and 42b of the receiving collar 46 and attachment body 40 of the primary trocar coupler 24, the tube 22b, the passageway 21b of the first coupling 20 of the valve assembly 14, the passageway 33b of the third coupling 32, the tube 34b of third elongate trifurcated tube 34, and back through the port 15 to the fluid source 12. The supply of pressurized gas to the primary trocar assembly 16 flows through one or more nozzles, preferably formed at a proximal end of and in fluid communication with the chamber of the primary trocar assembly 16, and is directed downward to form a fluidic/pneumatic seal therein and an effective barrier to proximal egress of gas from the abdominal cavity of the patient and maintain the pneumoperitoneum formed therein as described in the applications and patents cited above and incorporated by reference herein. The gas retrieved from the primary trocar assembly 16 recirculates gas that would otherwise exit through the opening 19 of the primary trocar assembly 16.

Importantly, while pressurized fluid from the passageway 33a of the third coupling 32 of the valve assembly 14 flows to both the passageway 21a of the first coupling 20 and the passageway 27a of the second coupling 26, the valve 38 is maintained in the first operating position 39, thus keeping the passageway 27a of the second coupling 26 fluidly isolated from the tube 28a. Thus, no pressurized fluid flows to the second elongate bifurcated tube 28 with the valve 38 disposed in the first operating position.

Surgical instruments and/or recording devices such as a camera are optionally translated through the cannula of the primary trocar assembly 16 via the opening 19 into the patient's abdomen as needed. Pressurized fluid continues to flow through the pressure/feed line 22a and vacuum return line 22b via the fluid path described above in quantities and at pressure levels dictated by the controller 13 to maintain the fluidic seal in the primary trocar assembly 16 and the abdominal pressure in the abdominal cavity. The controller 13 continually monitors, and if necessary, adjusts pressure in the abdominal cavity via the sense/insufflation tube 34c (which, as discussed above, is fluidly coupled to the tube 23c), as well as pressure in the pressure line 34a, which is fluidly coupled to the tube 22a, to maintain the fluidic/pneumatic seal.

The abdominal wall 102 is then punctured at a second location 105 using the secondary trocar assembly 18, which preferably also includes a cannula and obturator. The obturator is slidably inserted and translated through an opening 25 in a proximal end 18a of the secondary trocar assembly 18, and into and through the abdominal wall 12 at the second location 105. The distal end 18b of the secondary trocar assembly 18 is then inserted through the incision in the abdominal wall 102 made by the obturator. A frictional fit/seal between outer diameter of obturator and an inner diameter of the cannula prevents desufflation through the secondary trocar assembly 18.

The end 29 of the second elongate tube 28 is then attached to the secondary trocar assembly 18 using the secondary trocar coupler 30, thereby fluidly coupling each of the tubes 28a, 28b of the second elongate tube 28 with a chamber of the cannula of the secondary trocar assembly 18 (e.g., tubes 28a, 28b, which respectively correspond to the pressure/feed line and the vacuum/return line), are placed in fluid communication with the chamber of the cannula of the secondary trocar assembly 18 for, respectively, creation of a fluidic/pneumatic seal within the chamber and return/recirculation of gas that would otherwise exit through the opening 25 of the secondary trocar assembly 18.

The valve 38 is then manipulated to the second operating position of FIG. 10 by rotation of one of the top and bottom handles 88, 90, thus fluidly coupling the tubes 28a, 28b with the passageways 27a, 27b of the second coupling 26, which are fluidly coupled to the passageways 33a, 33b of the third coupling 32, whereby pressurized fluid from the fluid source 12 routed through the tube 34a is directed toward both the primary trocar assembly 16 and the secondary trocar assembly 18. In particular, pressurized fluid (e.g., $CO_2$ gas) continues to flow to the primary trocar assembly 16 through the same fluid path described above, but is no longer blocked at the second coupling 26 by the valve 38, and thus also flows through the passageway 27a, the tube 28a, the passageway 52a of the attachment body 50 of the secondary trocar coupling 30, the passageway 58a of the receiving collar 56, and, once the obturator of the secondary trocar assembly 18 is removed, into the chamber of the secondary trocar assembly 18.

Pressurized gas is simultaneously retrieved from the chamber of the secondary trocar assembly 18 via the tube 28b. In particular, the retrieved pressurized gas flows from the chamber of the secondary trocar assembly 18, through the passageways 58b and 52b of the receiving collar 56 and attachment body 50 of the secondary trocar coupler 30, the tube 28b, the passageway 27b of the second coupling 26, the passageway 33b of the third coupling 32, and the tube 34b of third elongate trifurcated tube 34 to the fluid source 12. The supply of pressurized gas flows through one or more nozzles, preferably formed at a proximal end of and in fluid communication with the chamber of the secondary trocar assembly 18, and is directed downward to form a fluidic/pneumatic seal therein and an effective barrier to proximal egress of gas from the abdominal cavity of the patient and maintain the pneumoperitoneum formed therein. Surgical instruments and/or recording devices such as a camera are then optionally translated through the cannula of the secondary trocar assembly 18 via the opening 25 into patient's abdomen as needed. Pressurized fluid continues to flow through the pressure/feed line 28a and vacuum return line 28b to maintain the fluidic seal therein. The controller 13 continually monitors, and if necessary, adjusts pressure in the abdominal cavity via the sense/insufflation tube 34c (which, as discussed above, is fluidly coupled to the tube 23c), as well as pressure in the pressure and vacuum lines 34a, 34b, which are fluidly coupled to the tubes 22a, 22b, to maintain the fluidic pneumatic seal.

Importantly, with the valve 38 disposed in the second operating position of FIG. 10 (designated by the handle position 41 of FIG. 13), pressurized fluid supplied from the fluid source 12 through the port 15 diverges within the manifold 6 to the first and second trocar assemblies 16, 18, and pressurized fluid retrieved from the first and second trocar assemblies 16, 18 converges within the manifold 6 and is routed back through the port 15. In this manner, and it is to be appreciated in accordance with illustrated embodiments of the invention, pressurized fluid can be selectively routed to and retrieved from multiple trocar assemblies using a single port 15 without requiring continuous flow through more than one trocar assembly. In addition, the use of multiple trocar assemblies in conjunction with the valve assembly of the present invention allows for better sealing, greater flexibility in terms of the number of surgical instruments which can be utilized simultaneously, and greater efficiency in terms of setup time and operation.

It will be appreciated that additional (e.g., third, fourth, fifth, etc.) trocar assemblies may be added to the system 10 by utilizing additional valves and further splitting the pressure/feed and vacuum/return lines of the valve assembly 14. However, it is preferred that sensing of the abdominal cavity be done with a single trocar assembly (e.g., the primary trocar assembly 16).

It is also to be appreciated that the pressure and return lines 28a, 28b of the bifurcated tube 28 could be configured to mechanically and fluidly coupled to a standard trocar known in the art via a leur lock assembly. In this manner, a standard trocar could be used in conjunction with the present system 10.

It is also anticipated that the valve assembly could be configurable to a third operating position which prevents pressurized fluid from flowing to the primary and secondary trocar assemblies, as well as any additional trocar assemblies coupled to the valve assembly 14. For example, it is anticipated that a secondary valve, similar or different from the valve 38, could be coupled to the third coupling 32 and configurable to block pressurized fluid flowing through the tube 34c from reaching either of the first and second elongate tubes 20, 28.

The above presents a description of a best mode contemplated for carrying out the present invention, and of the manner and process of making and using the present invention, in such full, clear, concise, and exact terms as to enable any person skilled in the art to which it pertains to make and use these devices and methods. The present invention is, however, susceptible to modifications and alternative method steps from those discussed above that are fully equivalent. Consequently, the present invention is not limited to the particular embodiments disclosed. On the contrary, the present invention encompasses all modifications and alternative constructions and methods coming within the spirit and scope thereof.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function, it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for providing pressurized fluid to trocar assemblies, the method comprising the steps of:
   (a) introducing a primary trocar assembly into an abdominal cavity of a patient;
   (b) introducing at least a secondary trocar assembly into the abdominal cavity of the patient;
   (c) providing a valve assembly;
   (d) coupling the valve assembly to the primary trocar assembly; the secondary trocar assembly, and a source of pressurized fluid;
   (e) selectively controlling a flow of pressurized fluid from the source to the trocar assemblies through operating the valve assembly in first and second operating positions, wherein the first operating position directs pressurized fluid from the source to flow to the primary trocar assembly while preventing pressurized fluid from the source from flowing to at least the secondary trocar assembly, and wherein the second operating position directs pressurized fluid from the source to flow to both the primary trocar assembly via the first coupling and at least the secondary trocar assembly;
   wherein the valve assembly has first, second, and third couplings; and
   wherein the first coupling of the valve assembly defines three passageways, and one of the three passageways is placed in fluid communication with the primary trocar assembly for directing the insufflation gas to the primary trocar assembly while the other two of the three passageways are fluidly isolated from the primary trocar assembly during insufflation of the abdominal cavity of the patient.

2. A method according to claim 1, further including the step of insufflating the abdominal cavity of the patient with the valve assembly in the first operating position, wherein insufflation gas is directed from the source to the primary trocar assembly with sufficient pressure to insufflate the abdominal cavity of the patient.

3. A method according to claim 1, wherein the first coupling of the valve assembly is coupled to the primary trocar assembly, the second coupling of the valve assembly is coupled to the secondary trocar assembly, and the third coupling of the valve assembly is coupled to the source of pressurized fluid.

4. A method according to claim 1, further including the step of providing pressurized fluid to the primary trocar assembly to create a pneumatic seal in the primary trocar assembly with the valve assembly in the first operating position.

5. A method according to claim 4, further including the step of providing pressurized fluid to the second trocar assembly to create a pneumatic seal in the secondary trocar assembly with the valve assembly in the second operating position.

6. A method according to claim 1, wherein the second coupling of the valve assembly defines two passageways, and at least one of the two passageways of the second coupling is placed in fluid communication with the secondary trocar assembly.

\* \* \* \* \*